United States Patent
Shcherbina et al.

(10) Patent No.: US 6,315,761 B1
(45) Date of Patent: Nov. 13, 2001

(54) INJECTION DEVICE WITH BELLOWED RESERVOIR

(75) Inventors: Alexis Shcherbina, Ubeles Street 5/1-54, Riga, LV 1073 (LV); Alexander Rudzits, Jurmala (LV)

(73) Assignee: Alexis Shcherbina, Riga (LV)

( * ) Notice: Subject to any disclaimer, the term of this patent is extended or adjusted under 35 U.S.C. 154(b) by 0 days.

(21) Appl. No.: 09/408,776

(22) Filed: Sep. 29, 1999

(51) Int. Cl.$^7$ .................................................. A61M 5/178
(52) U.S. Cl. ........................ 604/216; 604/212; 604/195; 604/185
(58) Field of Search ..................................... 604/185, 192, 604/195, 198, 199, 212, 216, 215, 217, 110, 181, 187, 272; 128/919

(56) References Cited

U.S. PATENT DOCUMENTS

| | | | |
|---|---|---|---|
| 3,557,788 | * | 1/1971 | Swartz . |
| 3,938,514 | * | 2/1976 | Boucher . |
| 4,753,638 | * | 6/1988 | Peters . |
| 4,883,466 | * | 11/1989 | Glazier . |
| 5,197,953 | * | 3/1993 | Colonna . |
| 5,318,547 | * | 6/1994 | Altschuler . |
| 5,382,235 | * | 1/1995 | Sak . |

FOREIGN PATENT DOCUMENTS

WO 93/09826   5/1993   (WO) .

* cited by examiner

*Primary Examiner*—Richard K. Seidel
*Assistant Examiner*—LoAn H. Thanh
(74) *Attorney, Agent, or Firm*—Malcolm D. Reid; Cecilia M. Jaisle

(57) ABSTRACT

Devices for injection of medicines into a human body are designed for one-time use during inpatient or outpatient treatment. The reuse of an injection device having a bellows 3 as an injection container is prevented by providing a locking attachment which prevents backward motion of a bottom 4 of the bellows 3 and which is mounted on elements of the device brought together during the injection (the bottom 4 of the bellows 3 and the housing/needle holder 1). A locking attachment is made in a form of a pair of interacting elastically deformable hooks 6 with a beveled catch and a female part in the form of a hole 7 with a ledge 8. At the instant the injection is completed, the sharpened end 10 of the needle 2 punctures a partition 9 in the bottom 4 of the bellows 3, further preventing reuse.

4 Claims, 1 Drawing Sheet

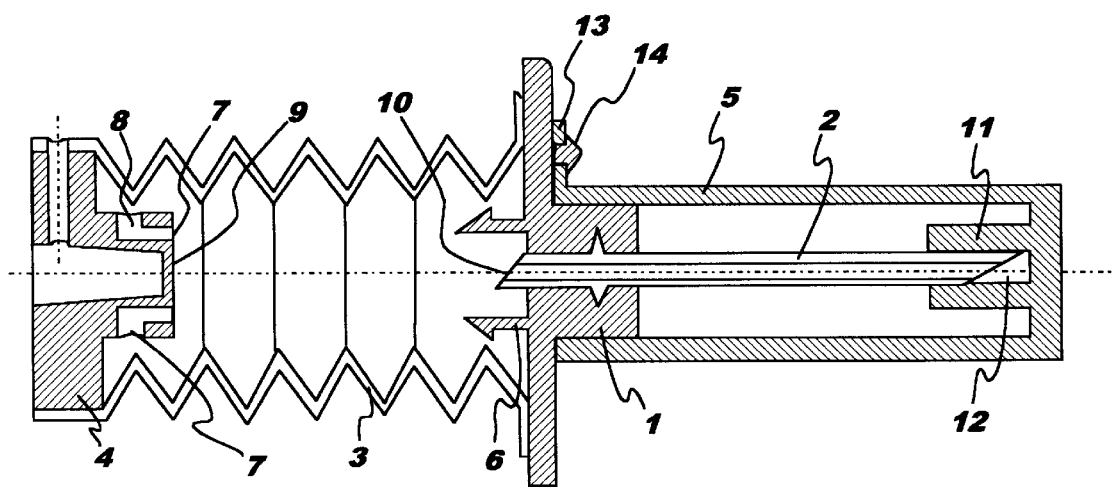

INJECTION DEVICE WITH BELLOWED RESERVOIR

This application claims the benefit of priority under 35 U.S.C. 119 of the Latvian application for patent filed Oct. 19, 1998 and assigned the number P-98-222.

FIELD OF THE INVENTION

This invention relates to a device for injection of medicine into a human body and is designed for one-time patient use during inpatient or outpatient treatment.

BACKGROUND OF THE INVENTION

Popular injection devices are inexpensive devices with a deformable plastic container filled with a medicine and used in place of piston syringes. Such devices, as described for example, in application WO 93/09826, used as a prototype, contain a needle pressed into a housing of a device, the passage of which connects with a cavity of a plastic container. By squeezing the plastic container, a medicine runs under pressure into a patient's body.

The drawback of these devices is the possibility of their uncontrollable reuse.

BRIEF DESCRIPTION OF THE INVENTION

The object of the present invention is to prevent the reuse of the device with a deformable injection container, such as the device described in application WO 93/09826.

This object is attained through the use of an injection container made in the form of a bellows with an open end hermetically connected with the end surface of a housing/needle holder. The bottom of the bellows and the part of the end surface enveloped by the bellows of the housing/needle holder are mutually brought together and are fitted with locking elements forming a permanent connection after an injection is given.

The locking elements may be in the form of a pair of interacting elastically deformable hooks with a beveled catch and a female part in the form of a hole with a ledge.

An additional method to prevent the reuse of this injection device may be provided by making a thin partition in the bottom of the bellows, the center of which positions on the geometric axis of the needle. The inner end of the needle is sharpened and protruded from the housing/needle holder towards the bottom of the bellows.

BRIEF DESCRIPTION OF THE DRAWING

FIG. 1 depicts an axial section view of the injection device of this invention.

DETAILED DESCRIPTION OF THE INVENTION

The device consists of the housing/needle holder 1 with the needle 2, the injection container in the form of the bellows 3 with the bottom 4 and the protective cap 5.

On the part of the housing/needle holder 1 enveloped by the bellows 3, there are hooks 6 made of elastically deformable material with beveled catches in relation to which holes 7 with ledges 8 are in the bottom 4 of the bellows.

At the center of the bottom 4 of the bellows, there is a thin partition 9 separating the cavity of the bellows 3 from the atmosphere. The center of the partition 9 is in line with the needle 2. The inner end or proximal 10 of the needle 2 is sharpened and protrudes towards the bottom 4 of the bellows 3.

The protective cap 5 in the inner part is provided with a plug 11, with a center hole 12 equal in diameter to the needle 2. On the outside of the protective cap 5 there is a loop 13 slipped over a latch 14.

Assembly and filling of the injection device may be performed in the following sequence. The protective cap 5 slips over the housing/distal needle holder 1 so that the end of the needle 2 tightly fits in the hole 12 of the plug 11 preventing effluence of medicine during storage. The loop 13 of the cap 5 slips over the latch 14 forming a permanent connection. One end of the bellows 3 hermetically joins with the housing/needle holder 1, for example, by means of adhesive or by hot crimping. After the bellows 3 is filled with the predetermined dose of a medicine, the other end of the bellows 3 is closed at the bottom 4 and sealed. A consumer receives it in such a form.

When the injection is needed, the loop 13 is cut and the cap 5 is removed. Upon insertion of the needle 2 into a patient's body, the injection is given by bearing on the bottom 4 as the result of which a medicine is injected into a patient's body from the cavity of the bellows 3 along the passage of the needle 2. Upon completion of the injection, hooks 6 enter holes 7 of the bottom 4 simultaneously with their squeezing out by the surface of the holes 7 and, while straightening, catch the ledge 8 in the hole 7, forming a permanent connection. This prevents the possibility of backward motion of the bottom 4 and the extension of the bellows 3. At the same time, the sharpened end 10 of the needle 2 punctures the partition in the bottom 4 breaking the tightness of the inner cavity of the bellows 3.

It is not intended that the scope of this invention should be limited other than as required by the following claims.

What is claimed is:

1. An injection device consisting of:

a needle, a housing/needle holder, and an injection-container, wherein the injection container is made in a form of a bellows, an open end of which is connected with the housing/needle holder, while a bottom of the bellows and a part of the housing/needle holder enveloped by the bellows are provided by locking elements forming a permanent connection preventing extension of the bellows upon completion of an injection, the locking elements made in a form of pairwise interacting elastically deformable hooks with a beveled catch and a female part in a form of a hole with a ledge; and wherein the bottom of the bellows has a partition separating the bellows from external atmosphere, a center of the partition is on a geometric axis of the needle, and a proximal part of the needle is sharpened and protrudes from the housing/needle holder towards the partition, so that the proximal part of the needle pierces the partition upon completion of an injection.

2. An injection device comprising:

a needle, a housing/needle holder, and an injection-container, wherein the injection container is made in a form of a bellows, an open end of which is connected with the housing/needle holder, while a bottom of the bellows and a part of the housing/needle holder enveloped by the bellows are provided by locking elements forming a permanent connection preventing extension of the bellows upon completion of an injection; and wherein in the bottom of the bellows a partition is made separating the bellows from external atmosphere, a center of which is positioned on a geometric axis of the needle; and a proximal part of the needle is sharpened and protrudes from the housing/needle holder towards the partition in the bottom of the bellows, so that the proximal part of the needle pierces the partition upon completion of an injection.

3. An injection device comprising:

a needle, a housing/needle holder, and an injection-container, wherein the injection container is made in a form of a bellows, an open end of which is connected with the housing/needle holder, while a bottom of the bellows and a part of the housing/needle holder enveloped by the bellows are provided by locking elements in a form of pairwise interacting elastically deformable hooks with a beveled catch and a female part in a form of a hole with a ledge forming a permanent connection preventing extension of the bellows upon completion of an injection.

4. The device as defined in claim 3 wherein in the bottom of the bellows a partition is made separating the bellows from external atmosphere, a center of which is positioned on a geometric axis of the needle; and a proximal part of the needle is sharpened and protrudes from the housing/needle holder towards the partition in the bottom of the bellows, so that the proximal part of the needle pierces the partition upon completion of an injection.

* * * * *